United States Patent
Goble et al.

(10) Patent No.: US 7,255,696 B2
(45) Date of Patent: Aug. 14, 2007

(54) ELECTROSURGICAL INSTRUMENT

(75) Inventors: Colin C. O. Goble, South Oxfordshire (GB); Mark G. Marshall, Berkshire (GB)

(73) Assignee: Gyrus Group plc, Berkshire (GB)

( * ) Notice: Subject to any disclaimer, the term of this patent is extended or adjusted under 35 U.S.C. 154(b) by 371 days.

(21) Appl. No.: 11/028,551

(22) Filed: Jan. 5, 2005

(65) Prior Publication Data

US 2006/0111709 A1    May 25, 2006

(30) Foreign Application Priority Data

Nov. 24, 2004 (GB) ................. 0425843.0

(51) Int. Cl.
*A61B 18/14* (2006.01)
(52) U.S. Cl. .......................... 606/48; 606/50
(58) Field of Classification Search ............ 606/48, 606/50
See application file for complete search history.

(56) References Cited

U.S. PATENT DOCUMENTS

| | | | |
|---|---|---|---|
| 3,987,795 A * | 10/1976 | Morrison ............ | 606/48 |
| 3,991,764 A | 11/1976 | Incropera et al. | |
| 4,202,336 A | 5/1980 | van Gerven | |
| 4,228,800 A * | 10/1980 | Degler et al. ......... | 606/48 |
| 5,647,871 A | 7/1997 | Levine et al. | |
| 5,788,694 A | 8/1998 | Vancaillie | |
| 5,895,386 A * | 4/1999 | Odell et al. ......... | 606/50 |
| 6,074,389 A | 6/2000 | Levine et al. | |
| 6,206,876 B1 | 3/2001 | Levine et al. | |
| 6,503,248 B1 | 1/2003 | Levine | |
| 6,544,264 B2 | 4/2003 | Levine et al. | |
| 6,733,501 B2 | 5/2004 | Levine et al. | |

FOREIGN PATENT DOCUMENTS

| | | |
|---|---|---|
| EP | 0 246 350 A1 | 11/1987 |
| WO | WO96/18349 A2 | 6/1996 |
| WO | WO03/055402 A1 | 7/2003 |

OTHER PUBLICATIONS

International Search Report for International Application No. GB 0425843.0, 2005.
International Search Report for International Application No. GB 0425842.2, 2005.

* cited by examiner

*Primary Examiner*—Lee S. Cohen
(74) *Attorney, Agent, or Firm*—Nixon & Vanderhye PC

(57) ABSTRACT

An electrode assembly for an electrosurgical instrument, comprises a bipolar cutting blade, and fluid supply lines for directing a cooling fluid to the cutting blade, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

9 Claims, 10 Drawing Sheets

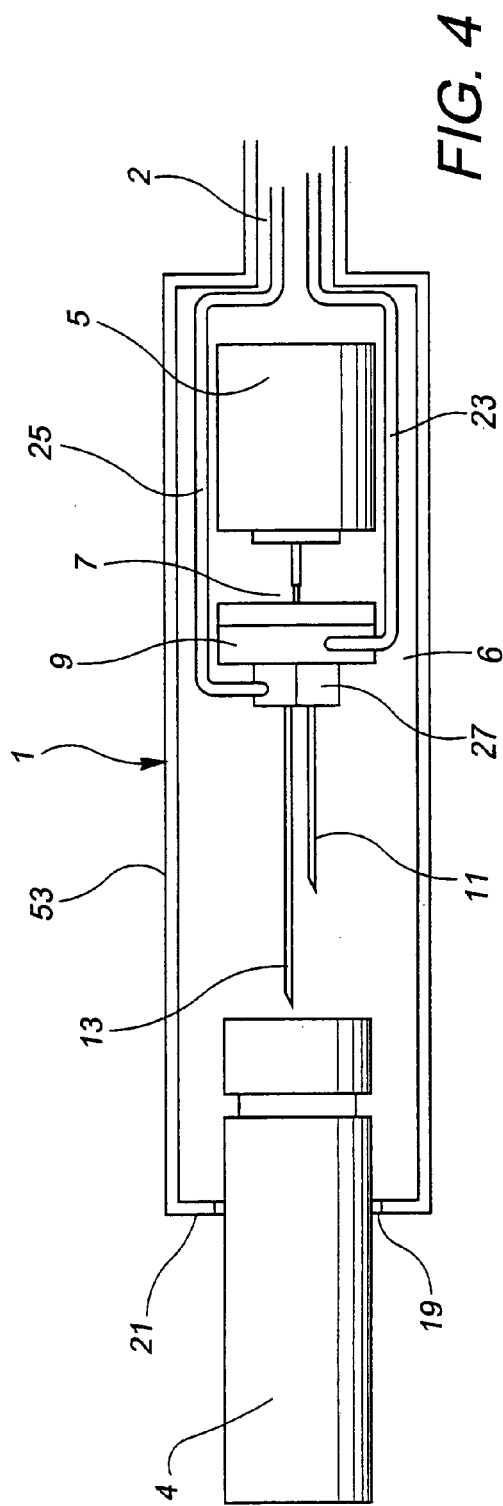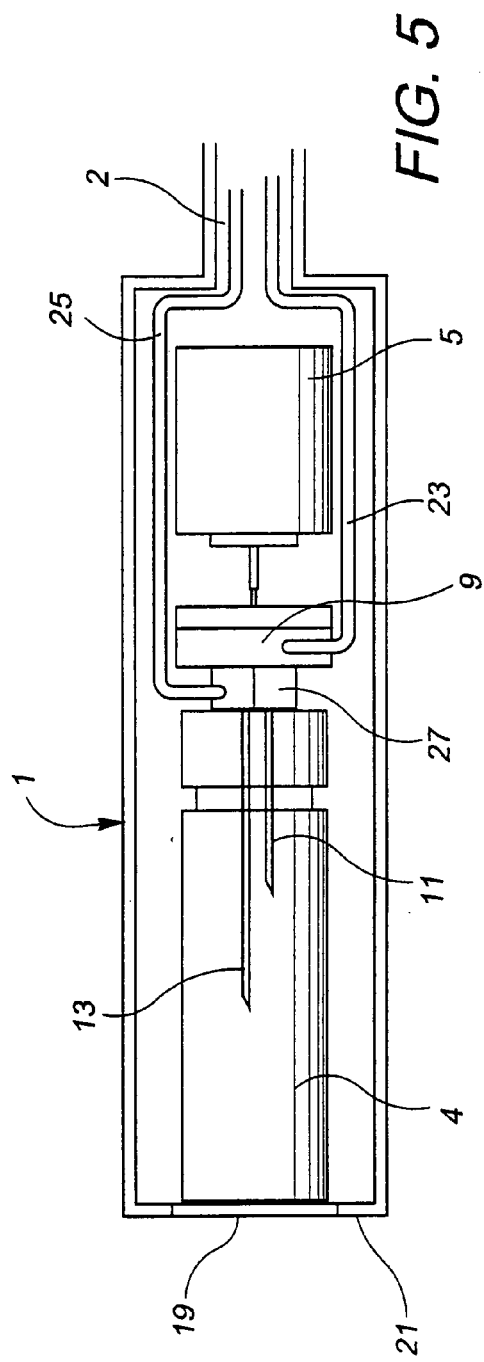
FIG. 4
FIG. 5

ELECTROSURGICAL INSTRUMENT

BACKGROUND OF THE INVENTION

This invention relates to an electrode assembly for an electrosurgical instrument. Such instruments are commonly used for the cutting and/or coagulation of tissue in surgical intervention, most commonly in "keyhole" or minimally-invasive surgery, but also in "open" or "laparoscopic assisted" surgery.

It is known to provide an electrosurgical instrument with a cooling system for prevention excess temperatures being developed at the electrode or electrodes. These fall into two categories. The first category includes instruments with a circulating cooling fluid. Examples are U.S. Pat. No. 3,991,764, U.S. Pat. No. 4,202,336, U.S. Pat. No. 5,647,871 and EP 0246350A. It should be noted that, with each of these systems, some or all of the fluid reservoir, pump and fluid supply lines are located externally of the electrosurgical handpiece. The second category includes instruments with heat pipes. Examples are U.S. Pat. No. 6,733.501, U.S. Pat. No. 6,544,264, U.S. Pat. No. 6,503,248, U.S. Pat. No. 6,206,876, and U.S Pat. No. 6,074,389.

BRIEF SUMMARY OF THE INVENTION

It is an aim of the present invention to provide an improvement over these prior art electrosurgical devices.

Accordingly, there is provided an electrode assembly for an electrosurgical instrument, the electrode assembly comprising a bipolar cutting blade, and fluid supply lines for directing a cooling fluid to, and from, the cutting blade, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

The cutting blade preferably comprises three electrodes in a sandwich structure with insulting layers therebetween. In a preferred arrangement the electrode assembly is as described in our co-pending published patent application EP 1458300.

Preferably, one or both of the first and third electrodes includes a lumen though which the cooling fluid is constrained to flow. According to one convenient arrangement, one or both of the first and third electrodes comprises a hollow structure, the inside of the hollow structure defining the lumen though which the cooling fluid is constrained to flow.

In this way, the cooling fluid is in intimate contact with the electrode assembly, especially the outer electrodes which are used for the coagulation of tissue. Cooling of the electrodes is particularly advantageous in the coagulation of tissue, as the coagulation power that can be used is otherwise limited by the rise in temperature of the electrodes. If the temperature of the electrodes is allowed to rise, tissue and dried blood will start to adhere to the electrodes, limiting the effectiveness thereof. This problem generally limits the available coagulation power of such electrodes, and cooling allows higher power and/or the longer use of coagulation electrodes without the temperature of the electrode reaching a level at which matter adhering becomes a problem.

The invention further provides an electrosurgical instrument comprising a handpiece, a bipolar cutting blade secured to the handpiece, and fluid supply lines for directing a cooling fluid to, and from, the cutting blade, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

Preferably, the housing also contains a reservoir of cooling fluid, and a pump for driving the cooling fluid through the supply lines. The cooling fluid is an electrically non-conductive fluid, typically deionised water or ethanol. A non-conductive fluid is required because the fluid is in intimate contact with each of the electrodes, and would therefore provide leakage current pathways if it were electrically conductive.

Having the pump and fluid reservoir within the handpiece provides the advantages of a circulating cooling fluid system, without the requirement for additional coolant lines and equipment external to the instrument handpiece. The handpiece can be supplied together with a reservoir of cooling fluid, or alternatively this can be assembled within the handpiece immediately prior to the instrument being used. In a preferred arrangement the housing also contains a reservoir of cooling fluid, and there are two possible arrangements for the fluid reservoir, a first arrangement in which the reservoir is not connected to the fluid supply lines, and the second arrangement being in which the reservoir is connected to the fluid supply lines. In this way, the instrument can be supplied with all of the necessary components, and yet the reservoir need not be connected to the supply lines until the instrument is ready for use. This minimises the risk of contamination of the cooling fluid or the corrosion of other components by the fluid, thereby increasing the acceptable shelf-life of the instrument.

In one convenient arrangement the housing is such that the reservoir is movable between first and second positions, the first position being in which the reservoir is not connected to the fluid supply lines, and the second position being in which the reservoir is connected to the fluid supply lines. In this way, the fluid reservoir can be moved into position, e.g. by a sliding movement, either when the instrument is manufactured, or alternatively immediately prior to the first use of the instrument.

The pump is preferably driven by an electric motor, typically a synchronous motor. In one convenient arrangement, the electric motor constitutes the pump. The motor conveniently includes a spindle on which is provided a paddle, the paddle being rotated by the action of the motor. The rotation of the paddle causes the cooling fluid to be driven though the fluid supply lines. Other types of pump, including those known for use with electronic equipment such as computers, may be suitable for use with this electrosurgical instrument.

The invention further provides an electrosurgical system comprising a bipolar cutting blade, a handpiece to which the cutting blade is secured, an electrosurgical generator for supplying a radio frequency voltage signal to the cutting blade, fluid supply lines for directing a cooling fluid to, and from, the cutting blade, and a pump for driving cooling fluid through the fluid supply lines, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

BRIEF DESCRIPTION OF THE DRAWINGS

The invention will now be further described, by way of example only, with reference to the accompanying drawings, in which.

FIGS. 4 and 5 are sectional views of an alternative embodiment of handpiece forming part of the electrosurgical instrument of FIG. 1;

DETAILED DESCRIPTION OF THE INVENTION

Figure 1:
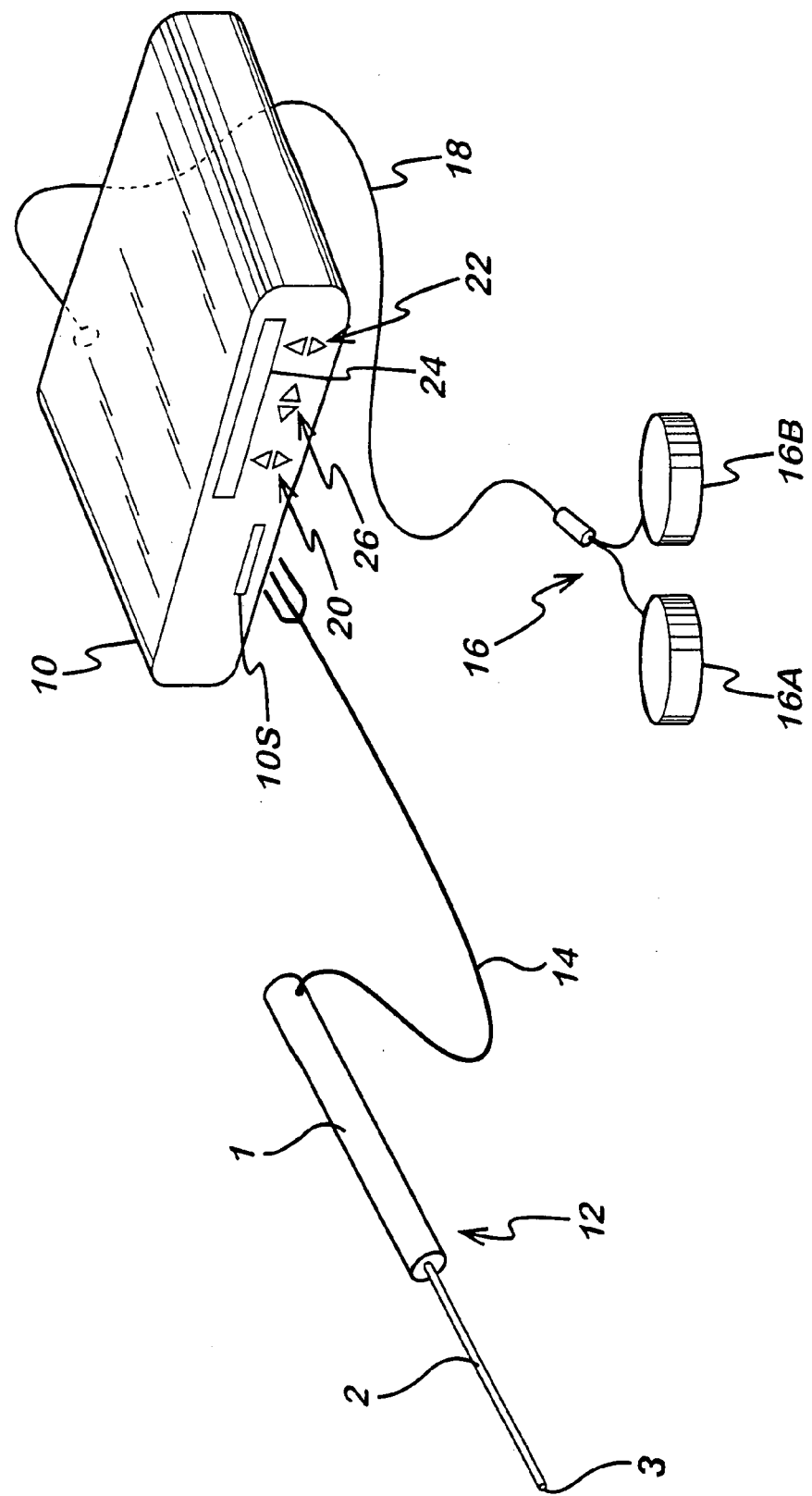
FIG. 1 is a schematic diagram of an electrosurgical system including an electrode assembly constructed in accordance with the present invention.

Referring to FIG. 1, a generator 10 has an output socket 10S providing a radio frequency (RF) output for an electrosurgical instrument 12 via a connection cord 14. Activation of the generator 10 may be performed from the instrument 12 via a connection cord 14, or by means of a footswitch unit 16, as shown, connected to the rear of the generator by a footswitch connection cord 18. In the illustrated embodiment, the footswitch unit 16 has two footswitches 16A and 16B for selecting a coagulation mode and a cutting mode of the generator 10 respectively. The front panel of the generator 10 has push buttons 20 and 22 for respectively setting parameters such as the coagulation and cutting power levels, which are indicated in a display 24. Push buttons 26 are provided as an alternative means for selection between coagulation and cutting modes.

Figure 2:
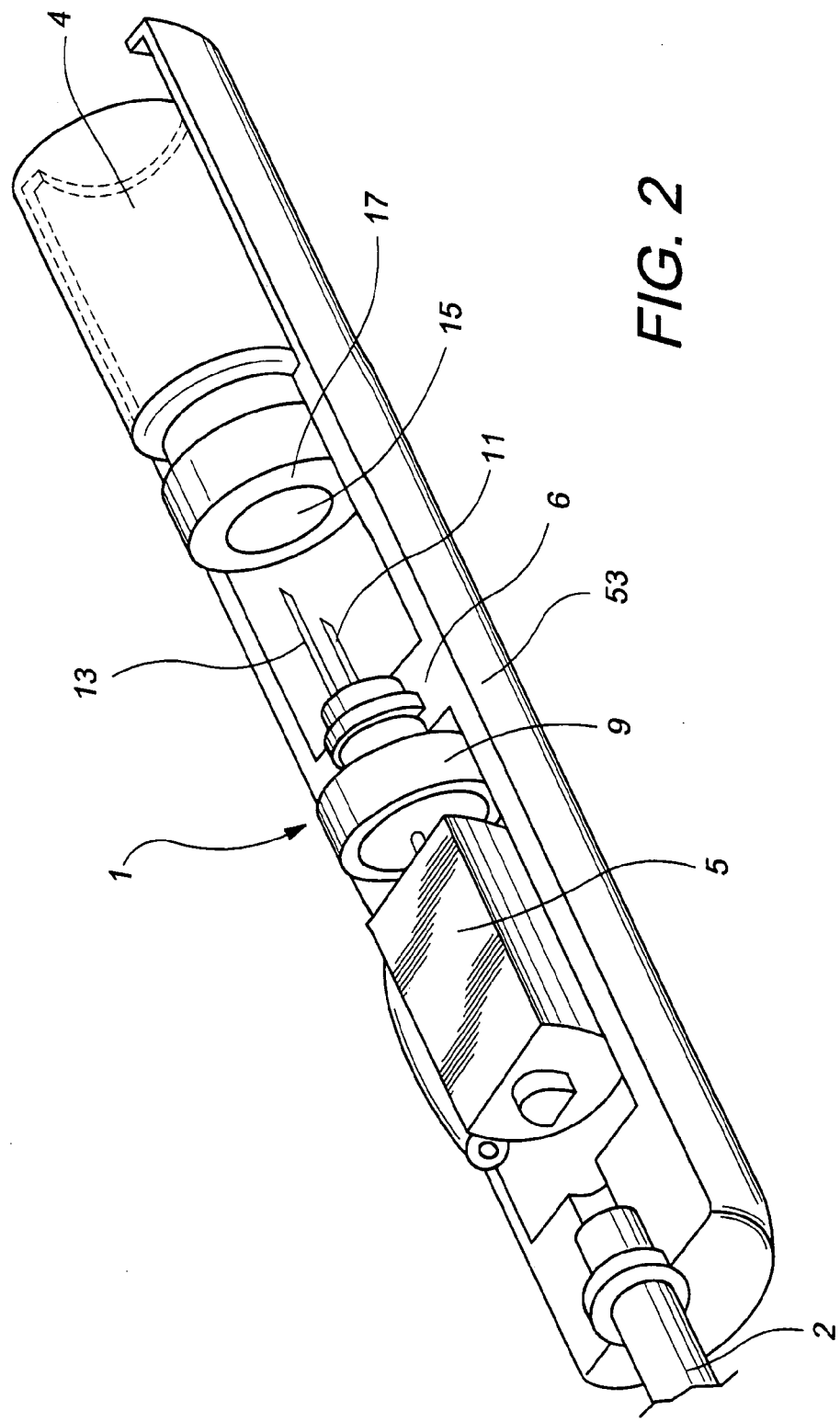
FIGS. 2 and 3 are views, shown partly in section, of a handpiece forming part of the electrosurgical instrument of FIG. 1.
Figure 6:
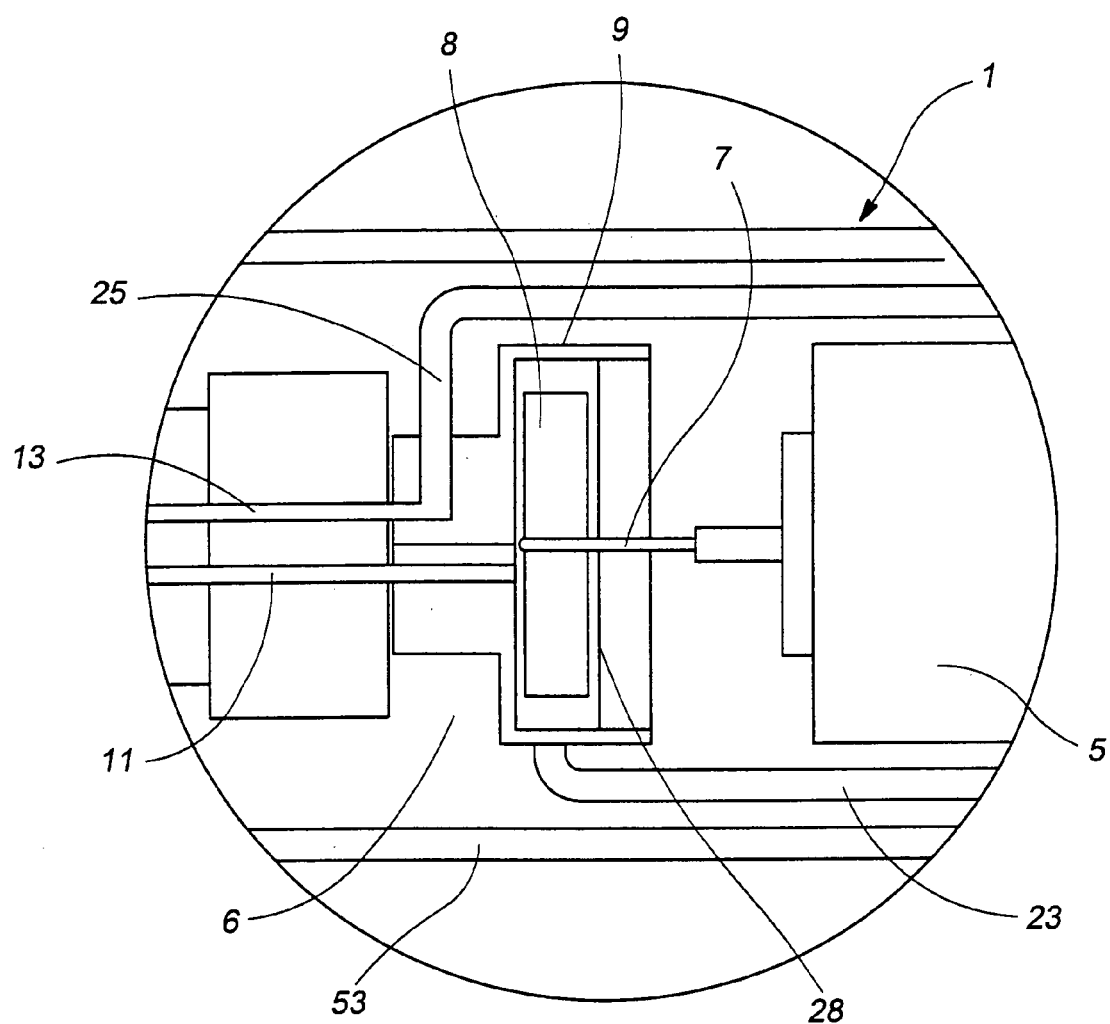
FIG. 6 is an enlarged sectional view of part of the handpiece of FIGS. 4 and 5.

The instrument 12 comprises a handpiece 1, a shaft 2 and an electrode assembly 3 mounted at the distal end of the shaft. Referring to FIG. 2, the handpiece 1 comprises a hollow housing 53, in which is located a fluid reservoir 4, a motor 5, and a connection block 6. Referring also to FIG. 6, the motor 5 includes a spindle 7, and a paddle wheel 8 attached to the spindle and located in a chamber 9 within the connection block 6. The connection block 6 also includes an inflow needle 11 and an outflow needle 13. The fluid reservoir 4 is slidable within the housing 53, between the position shown in FIG. 2 and that of FIG. 3, in which the inflow and outflow needles 11 and 13 pierce a diaphragm 15 present on the end face 17 of the fluid reservoir.

FIGS. 4 and 5 show an alternative version of the handpiece 1. In the handpiece 1 of FIGS. 4 and 5, the fluid reservoir 4 is introduced through an aperture 19 in the rear face 21 of the housing 53. FIGS. 4 and 5 also show a fluid feed line 23 and a fluid return line 25, which were omitted from FIGS. 2 and 3 for reasons of clarity. The fluid feed line 23 runs from the chamber 9, through the shaft 2, to the electrode assembly 3. The inflow needle 11 is in communication with the chamber 9, while the outflow needle 13 is in communication with fluid return line 25 at a section 27 of the connection block 6. The fluid return line 25 runs from the connection block 6, through the shaft 2, to the electrode assembly 3.

Referring to FIG. 6, the paddle wheel 8 is located in the chamber 9, and is mounted on the spindle 7, which spindle extends through a sealing membrane 28. The membrane 28 prevents cooling fluid from the chamber 9 entering the motor 5.

Figure 7:
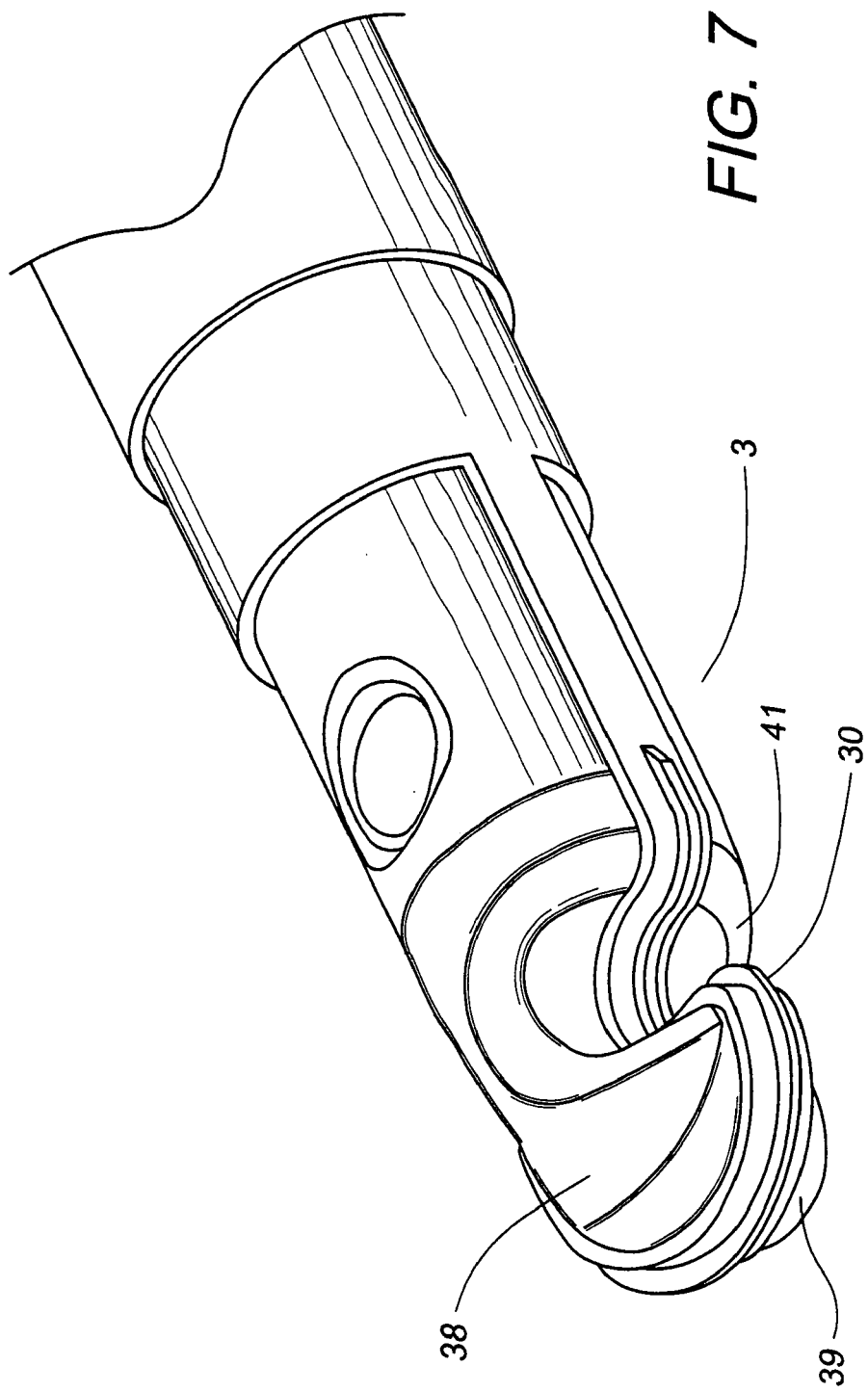
FIG. 7 is a perspective view of an electrode assembly forming part of the electrosurgical instrument of FIG. 1.
Figure 8:
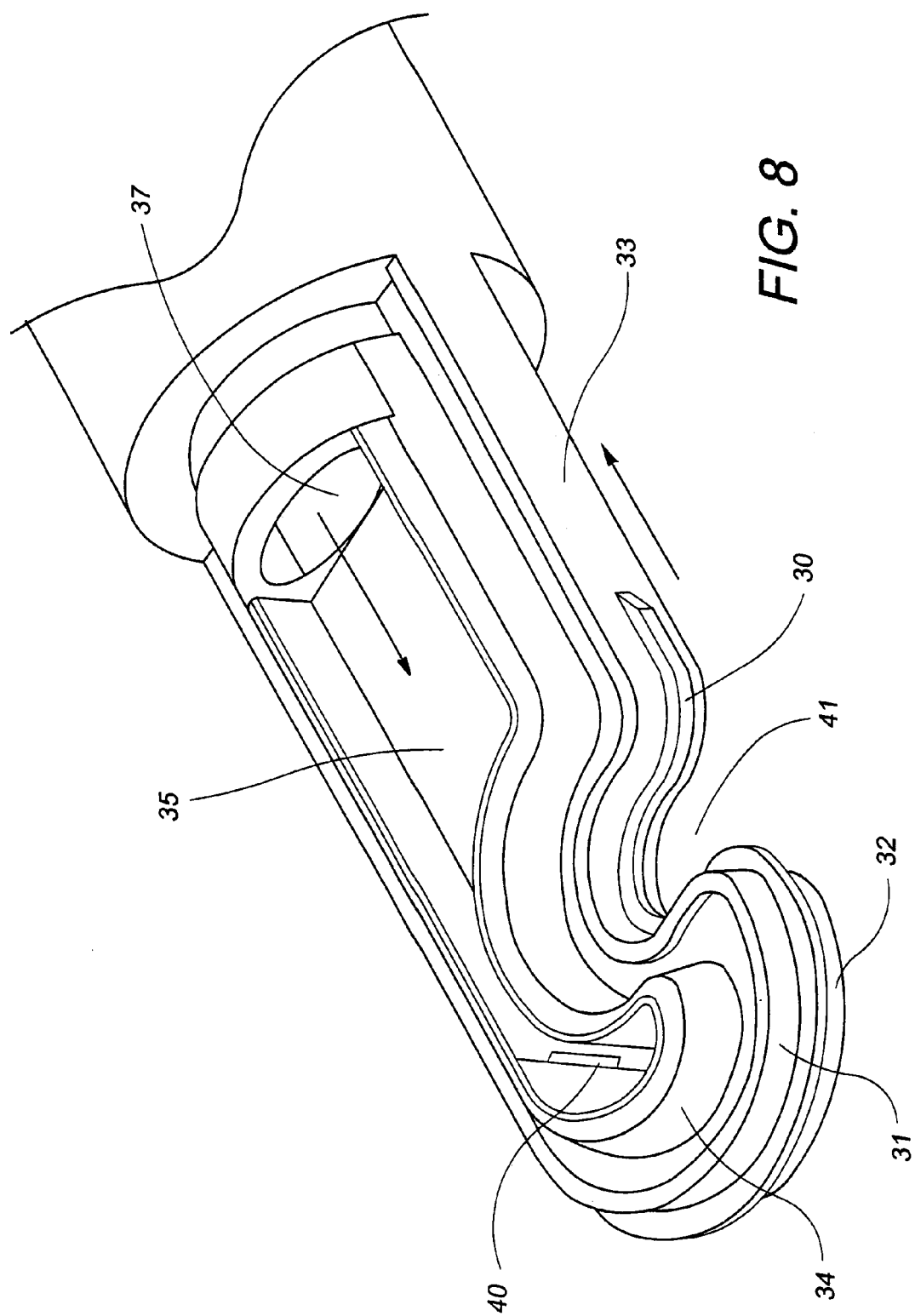
FIG. 8 is a perspective view, shown partly in section, of the electrode assembly of FIG. 7.
Figure 9:
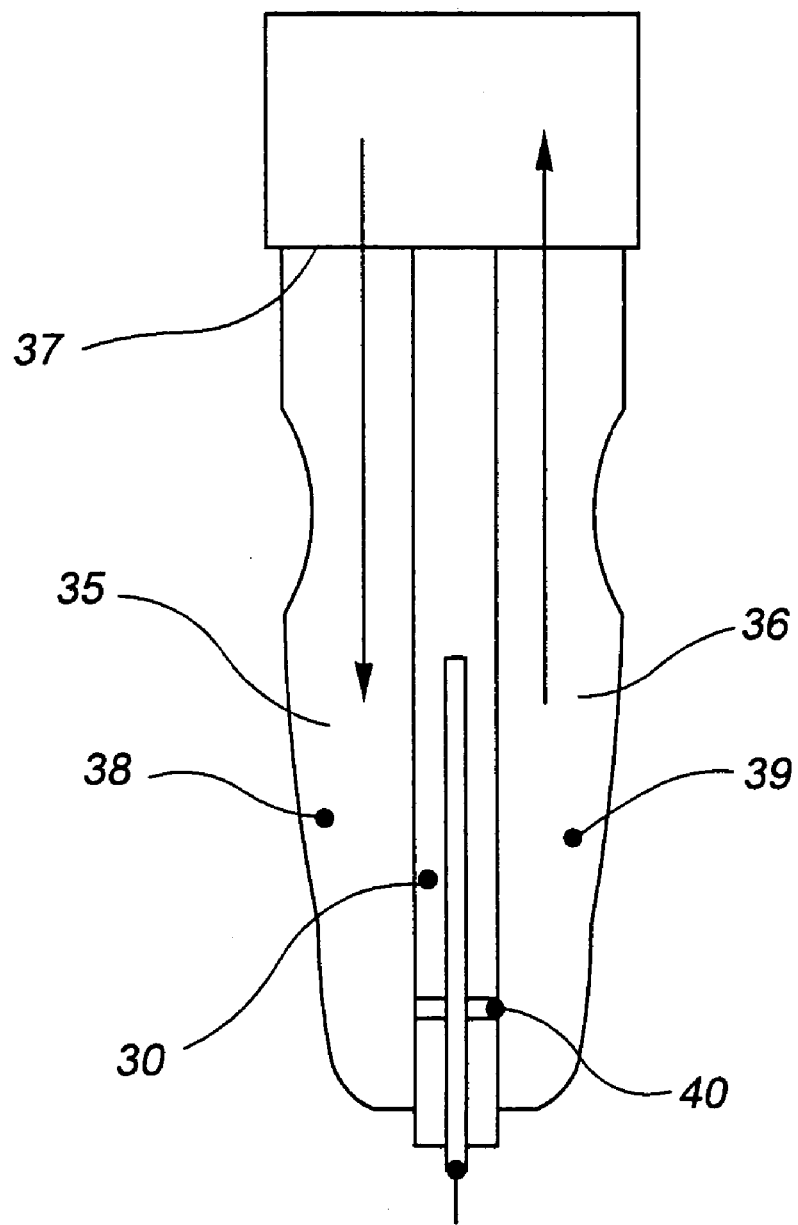
FIG. 9 is a schematic sectional plan view of the electrode assembly of FIG. 7.

The electrode assembly 3 will now be described with reference to FIGS. 7 to 9. At the centre of the electrode assembly is a flat active electrode 30, with insulating mouldings 31 and 32 on either side thereof. The insulating mouldings 31 and 32 are both part of an integrated moulding assembly 33. The insulating moulding 31 includes wall portions 34 defining a hollow space 35 therein, while the insulating moulding 32 has similar wall portions defining a hollow space 36. The moulding 31 is provided with an opening 37 connecting the hollow space 35 with the fluid feed line 23, while the moulding 32 is provided with a similar opening connecting the hollow space 36 with the fluid return line 25.

The mouldings 31 and 32 are covered by electrically-conductive shells 38 and 39, constituting return electrodes for the electrode assembly 3. The active electrode 30 is provided with a through hole 40, connecting the hollow spaces 35 and 36 beneath the return electrodes 38 and 39. The electrode assembly 3 is in the form of a hook arrangement, with a recess 41 provided in one side thereof.

Figure 10A:
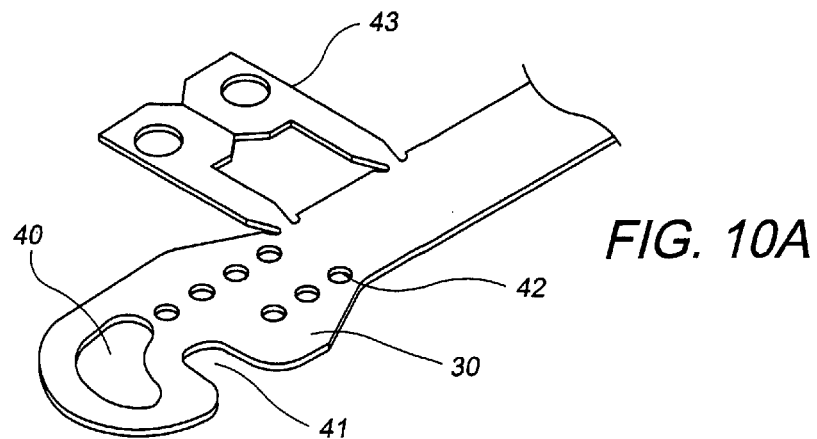
FIGS. 10A to 10F are perspective views showing the electrode assembly of FIG. 7 is various stages of assembly.

The assembly of the above construction will now be described with reference to FIGS. 10A to 10F. FIG. 10A shows the active electrode 30, formed by stamping from stainless steel. The stamped active electrode 30 has the through hole 40 formed therein, along with additional holes 42 provided for fastening purposes. The stamping also has ears 43, which are removed at the end of the manufacturing process, but which are provided for materials handling purposes.

Figure 10B:
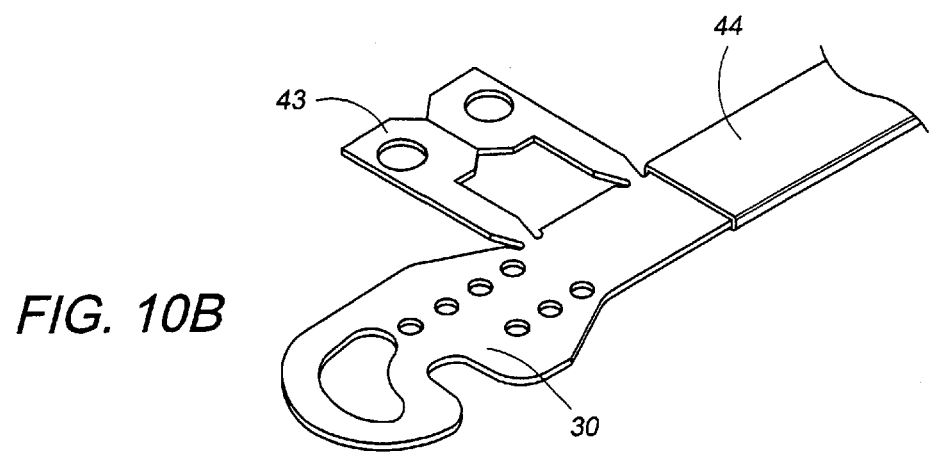
Figure 10C:
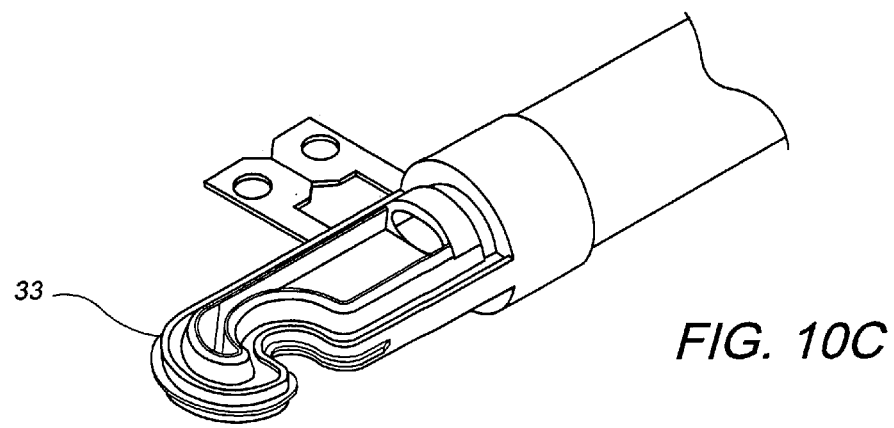
Figure 10D:
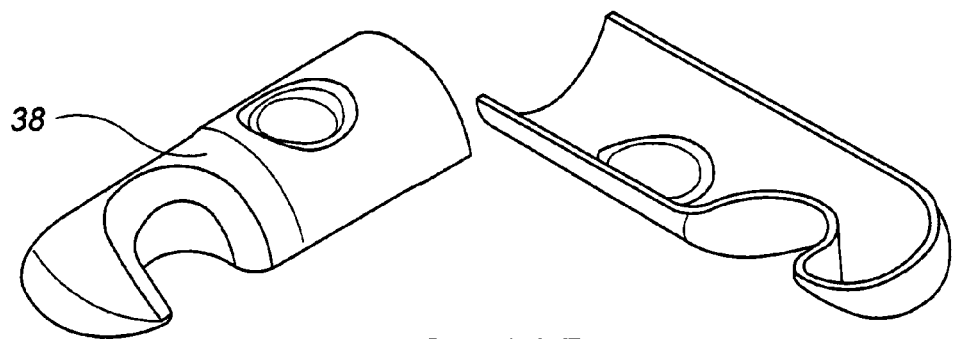
Figure 10E:
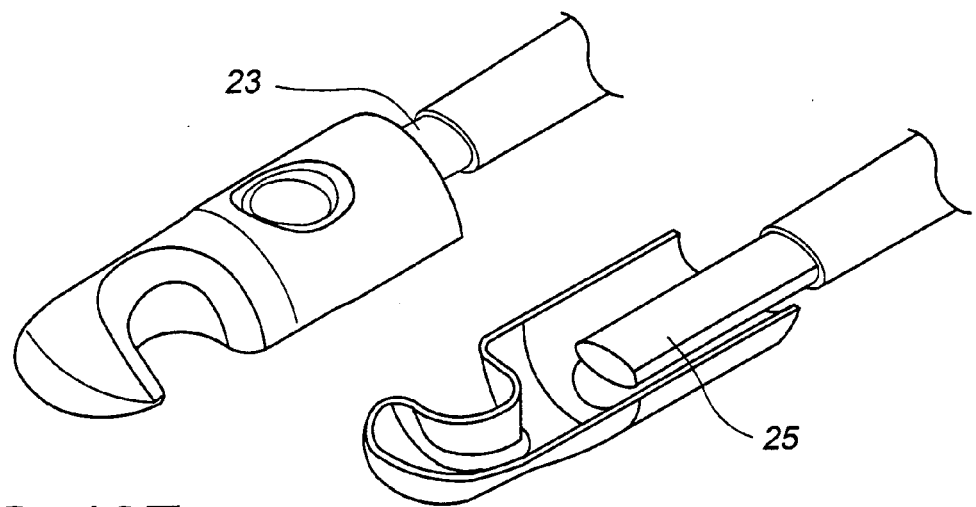
Figure 10F:
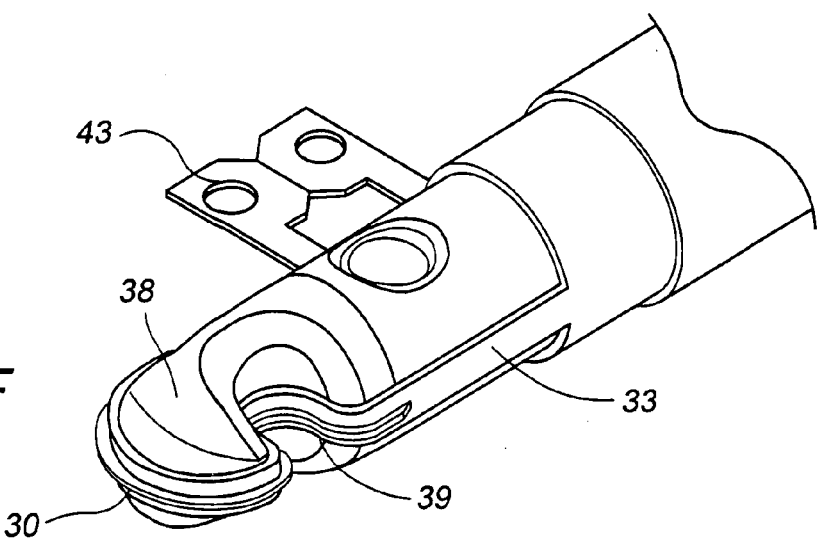

FIG. 10B shows heat-shrink material 44 added to the proximal portion of the active electrode 30. The active electrode 30 is then assembled into the integrated moulding assembly 33, as shown in FIG. 10C. The insulating moulding assembly 33 is formed of ceramic, or alternatively silicone rubber. The electrically-conductive shells 38 and 39 are formed of copper (see FIG. 10D), and are assembled on to the moulding assembly 33 by welding them on to the metallic fluid feed and return lines 23 and 25 respectively (see FIG. 10E). The completed assembly is shown in FIG. 10F, prior to the removal of the ears 43.

Figure 3:
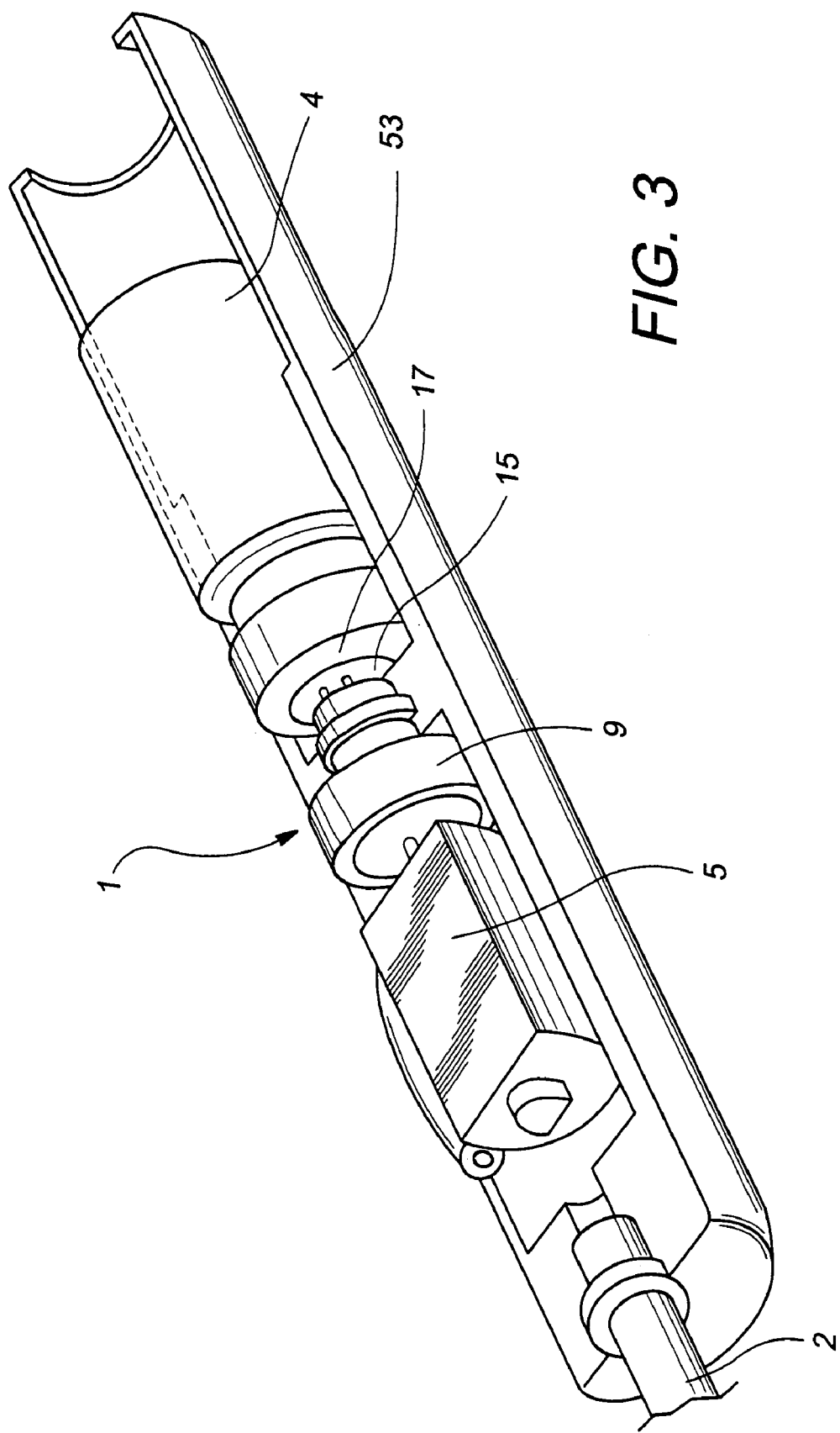

The operation of the instrument 12 is as follows. If not already in position, the fluid reservoir 4 is moved into location with the connection block 6, as shown in FIGS. 3 and 5. The instrument 12 is connected to the generator 10, and introduced into the surgical site. The footswitch 16 is operated in order to supply an electrosurgical RF voltage to the electrodes 30, 38 and 39 in order to cut or coagulate tissue at the surgical site. The operation of the electrodes 30, 38 and 39 is described in more detail in our published application EP 1458300, but in essence when electrosurgical cutting is required a cutting voltage is supplied between the cutting electrode 30 and one or both of the return electrodes 38 and 39. Alternatively, when electrosurgical coagulation is required, a coagulating voltage is supplied between the return electrodes 38 and 39. In a blended mode, a blended waveform typically consisting of a waveform rapidly alternating between the cutting and coagulating voltage is supplied, typically also rapidly alternating between the cutting and coagulating electrodes 30, 38 and 39. For clarity, the leads connecting the RF signal between the cord 14 and the electrode assembly 3 have been omitted, but the fluid feed and return lines 23 and 25 could be formed of an electrically-conductive material and used for this purpose.

When the footswitch 16 is depressed, a signal is also sent to the motor 5 which causes the spindle 7 and hence the paddle wheel 8 to rotate. The rotation of the paddle wheel 8 causes cooling fluid to be driven out of the chamber 9 and through the fluid feed line 23. The cooling fluid is typically an electrically non-conductive fluid such as deionised water or ethanol. The cooling fluid travels though the fluid feed line 23 along the shaft 2 to the hollow space 35 within the return electrode 38. Once within the hollow space 35, the cooling fluid travels through the active electrode 30 by means of the through hole 40, and into the hollow space 36 within the other return electrode 39. From the hollow space 36, the cooling fluid travels back along the shaft 2 by means of the fluid return line 25 and into the reservoir 4 via the outflow needle 11.

The circulating cooling fluid travels to, and from, the electrode assembly 3, coming into close contact with both return electrodes 38 and 39 and cooling them accordingly. By cooling the return electrodes 38 and 39, more electrical energy can be transferred into the tissue for coagulation purposes without the electrodes reaching a temperature at which tissue and blood will start to adhere to the electrode surfaces. It is essential that the cooling fluid is substantially electrically non-conductive, as it may come into contact with the active electrode 30 and with the return electrodes 38 and 39.

The motor 5 can be run continuously, or can be switched in and out whenever the electrode assembly 3 is actuated. In may be advantageous to run the motor 5, and hence circulate the cooling fluid, whenever the electrode assembly 3 is actuated, and for a predetermined additional time thereafter. In this way, any residual heat within the electrodes 30, 38 and 39, or transferred to the electrodes from adjacent hot tissue, will be removed by the cooling fluid.

It will be appreciated that the instrument 12 provides a handpiece 1 containing the fluid reservoir 4 and all of the fluid lines, and the only external lead is the connection cord 14 for the RF signal. This connection cord 12 can also be used for the electric supply to the motor 5. Alternatively, the RF signal can also be used as a supply for the motor 5. Heat is removed from the electrode assembly 3 by the cooling fluid, which is deposited back into the reservoir 4, and dissipated through the housing 53. For all normal operations of the instrument 12, the temperature rise of the housing 53 is only a few degrees, and still comfortable for the user of the instrument to hold.

By cooling the electrodes 30, 38 and 39, particularly during the coagulation of tissue, greater coagulative power can be applied without the overheating of the electrodes. Tissue sticking and the coating of the electrodes 30, 38 and 39 with dried blood are factors limiting the coagulative power of un-cooled instruments, and the present invention provides a compact and versatile instrument with considerable coagulative capabilities. In addition, the instrument, possibly even including the connection cord 14, can be made disposable, by the use of relatively-inexpensive components therein.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An electrode assembly for an electrosurgical instrument, the electrode assembly comprising a bipolar cutting blade, and fluid supply lines for directing a cooling fluid to, and from, the cutting blade, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

2. An electrode assembly according to claim 1, wherein the cutting blade comprises three electrodes in a sandwich structure with insulating layers therebetween.

3. An electrode assembly according to claim 2, wherein the second electrode is positioned between the first and third electrodes.

4. An electrode assembly according to claim 1, wherein one or both of the first and third electrodes includes a lumen though which the cooling fluid is constrained to flow.

5. An electrode assembly according to claim 4, wherein one or both of the first and third electrodes comprises a hollow structure, the inside of the hollow structure defining the lumen though which the cooling fluid is constrained to flow.

6. An electrosurgical instrument comprising a handpiece, a bipolar cutting blade secured to the handpiece, and fluid supply lines for directing a cooling fluid to, and from, the cutting blade, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

7. An electrosurgical instrument according to claim 6, wherein the housing also contains a reservoir of cooling fluid.

8. An electrosurgical instrument according to claim 7, wherein the cooling fluid is deionised water or ethanol.

9. An electrosurgical system comprising a bipolar cutting blade, a handpiece to which the cutting blade is secured, an electrosurgical generator for supplying a radio frequency voltage signal to the cutting blade, fluid supply lines for directing a cooling fluid to, and from, the cutting blade, and a pump for driving cooling fluid through the fluid supply lines, the cutting blade comprising first, second and third electrodes, and electrical insulators spacing apart the electrodes, the fluid supply lines being such that cooling fluid enters the cutting blade via the first electrode, passes through an aperture in the second electrode, and exits the cutting blade via the third electrode.

* * * * *